United States Patent
Ina

(10) Patent No.: US 6,369,263 B1
(45) Date of Patent: Apr. 9, 2002

(54) PROCESS FOR PRODUCING HYDROQUINONE DIESTER DERIVATIVE

(75) Inventor: Tomohide Ina, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/623,135

(22) PCT Filed: Dec. 24, 1999

(86) PCT No.: PCT/JP99/07246

§ 371 Date: Aug. 28, 2000

§ 102(e) Date: Aug. 28, 2000

(87) PCT Pub. No.: WO00/40540

PCT Pub. Date: Jul. 13, 2000

(30) Foreign Application Priority Data

Dec. 28, 1998 (JP) .............................. 10-372784

(51) Int. Cl.[7] .................. C07C 67/48; C07C 69/74; C07C 69/00; C07C 69/34
(52) U.S. Cl. .............. 560/78; 560/1; 560/127; 560/129; 560/190; 560/191
(58) Field of Search ................ 552/500; 560/1, 560/78, 127, 129, 190, 191

(56) References Cited

FOREIGN PATENT DOCUMENTS

| EP | 0850910 | * | 7/1998 |
| EP | A1850910 | | 7/1998 |
| EP | A1850912 | | 7/1998 |
| EP | 0916642 | * | 5/1999 |
| EP | A1916642 | | 5/1999 |
| EP | A1952137 | | 10/1999 |
| JP | A477632 | | 4/1972 |
| JP | A7179396 | | 7/1995 |
| JP | A9169696 | | 6/1997 |
| JP | A1053555 | | 2/1998 |

* cited by examiner

Primary Examiner—Alton Pryor

(57) ABSTRACT

A hydroquinone diester derivative represented by the formula (1):

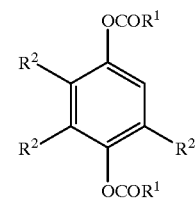

(1)

wherein $R^1$ and $R^2$ are the same or different, each representing an alkyl group, a cycloalkyl group, an aryl group, or a heterocyclic group is crystallized from a reaction mixture containing the hydroquinone diester derivative, and the resulting product in crystallized form is washed. A solvent for the crystallization is composed of an organic carboxylic acid and water, and the crystallized product is washed with warm or hot water of 40° C. or above. In the formula (1), $R^1$ and $R^2$ are $C_{1-4}$ alkyl groups.

11 Claims, No Drawings

PROCESS FOR PRODUCING HYDROQUINONE DIESTER DERIVATIVE

This application is the national phase under 35 U.S.C. §371 of PCT International Application No. PCT/JP99/07246 which has an International filing date of Dec. 24, 1999, which designated the United States of America.

TECHNICAL FIELD

The present invention relates to a process for producing hydroquinone diester derivatives.

BACKGROUND TECHNOLOGY

Hydroquinone diester derivatives (e.g., trimethylhydroquinone diesters, trimethylhydroquinone derived therefrom by hydrolysis) are useful as intermediates of medicines and also industrially important compounds, used as starting materials of vitamin E; antioxidants for resins, higher fatty acids, higher alcohols, fats, or oils; or polymerization inhibitors for polymerizable monomers.

Japanese Patent Application Laid-Open No. 7632/1972 (JP-A-47-7632) discloses a process of producing trimethylhydroquinone diesters by reacting 2,6,6-trimethylcyclohex-2-ene-1,4-dione (ketoisophorone, KIP) with an acylating agent in the presence of an acid catalyst (a protonic acid or a Lewis acid catalyst).

In this process, a pure trimethylhydroquinone diester is obtained by neutralizing the reaction mixture, extracting the reaction product, removing the acid catalyst by filtration, condensing the extract (filtrate) under reduced pressure, and then recrystallizing using hexane. Although its purification step is complicated, yet the yield of the trimethylhydroquinone diester is low. When hexane is employed as a solvent for recrystallization, the purity of the trimethylhydroquinone diester is improved only to a limited extent probably due to hexane's low solubility in by-products. This may be the reason why the melting points of trimethylhydroquinone diesters mentioned in the literature lie within the range of as wide as 97 to 107° C. In addition, hexane is a low-boiling point solvent and its solubility in the object compound is extremely low, which require hexane as the recrystallization solvent to be used in a large amount. Thus, when it comes to purification, the process is industrially disadvantageous.

Thus, an object of the present invention is to provide a process for obtaining a highly pure hydroquinone diester derivative from a reaction mixture through a simple procedure.

Another object of the present invention is to provide a process for producing a hydroquinone diester derivative in a high yield.

Still another object of the present invention is to provide a process for producing a highly pure hydroquinone diester derivative from a reaction mixture of a ketoisophorone derivative and an acylating agent in a high yield.

DISCLOSURE OF INVENTION

The inventors of the present invention made intensive and extensive studies to achieve the above objects, and finally found that a hydroquinone diester derivative can be crystallized directly from a reaction mixture of a ketoisophorone derivative and an acylating agent, and that a trimethylhydroquinone diester of high purity can be obtained with high yield by washing the crystallized product. The present invention is based on the above findings.

That is, in the process of the present invention, a hydroquinone diester derivative represented by the following formula (1):

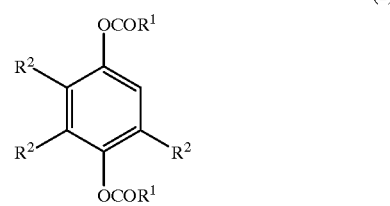

wherein $R^1$ and $R^2$ are the same or different, each representing an alkyl group, a cycloalkyl group, an aryl group, or a heterocyclic group is produced by crystallizing the derivative from a reaction mixture containing the hydroquinone diester derivative and then washing the crystallized product. The crystallized product may be washed with warm or hot water of 40° C. or above. Employed as a solvent to be used in the crystallization may be a combination of an organic carboxylic acid and water. In the formula (1), $R^1$ and $R^2$ may be $C_{1-4}$ alkyl groups. Especially, the hydroquinone diester derivative may be crystallized out from a reaction mixture which can be obtained by reacting a ketoisophorone derivative of the formula (2):

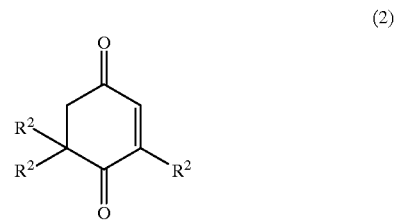

wherein $R^2$ has the same meaning as defined above with an acylating agent. A solid filtered out by washing the crystallized product may contain, on a solid matter basis, 0 to 2% by weight of a catechol diester derivative shown by the following formula (3):

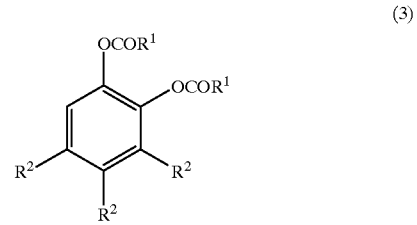

wherein $R^1$ and $R^2$ have the same meanings as defined above.

BEST MODE FOR CARRYING OUT THE INVENTION

[Reaction Mixture]

In the present invention, a hydroquinone diester derivative of the formula (1) is obtained by crystallization from a reaction mixture containing the hydroquinone diester derivative.

In the formulae (1) and (2), exemplified as the alkyl groups designated by $R^1$ and $R^2$ are $C_{1-10}$ alkyl groups (e.g., $C_{1-8}$alkyl groups such as methyl, ethyl, butyl, isobutyl, t-butyl, pentyl, hexyl group). Examples of the cycloalkyl group are $C_{3-10}$cycloalkyl groups (e.g., cyclohexyl group). As the aryl group, there may be exemplified $C_{6-12}$aryl groups (e.g., phenyl group, and substituted phenyl groups such as p-methylphenyl group). As the heterocyclic group, there may be mentioned aromatic or nonaromatic 5- or 6-membered heterocyclic groups having at least one hetero atom selected from nitrogen, oxygen and sulfur (e.g., furyl group, thienyl group, nicotinyl group, pyridyl group). In compounds represented by the formulae (1) and (2), the substituents $R^1$ and $R^2$ may be either the same or different.

Preferred as $R^1$ are $C_{1-8}$alkyl groups, particularly $C_{1-6}$alkyl groups (e.g., $C_{1-4}$alkyl groups such as methyl and ethyl group), and preferred as $R^2$ are $C_{1-4}$alkyl groups such as methyl group and ethyl group, with methyl group particularly preferred.

Exemplified as the hydroquinone diester derivative (1) are 2,5,6-tri$C_{1-4}$alkylhydroquinone diesters (particularly, 2,5,6-trimethylhydroquione diacetate (DAB)).

A reaction mixture containing such hydroquinone diester derivative (1) can be obtained by reacting a ketoisophorone derivative shown by the formula (2) with an acylating agent in the presence of a catalyst. In the formula (2), $R^2$ has the same meaning as defined for the formula (1).

As the ketoisophorone derivative (2), usually, 2,6,6-tri$C_{1-4}$alkylcyclohex-2-ene-1,4-diones (particularly, 2,6,6-trimethylcyclohex-2-ene-1,4-dione (ketoisophorone, KIP), can be used.

Either a protonic acid or a Lewis acid can be employed as the catalyst. Exemplified as the protonic acid are inorganic acids (e.g., sulfuric acid, hydrochloric acid, phosphoric acid, fluoroboric acid, hydrofluoric acid); organic acids (e.g., sulfonic acids such as p-toluenesulfonic acid, benzenesulfonic acid, methanesulfonic acid, ethanesulfonic acid; halocarboxylic acids such as chloroacetic acid, trichloroacetic acid and trifuluoroacetic acid; picric acid), and superstrong acids having a Hammett acidity function $H_0$ of smaller than −11.93 (e.g., $H_2SO_4$—$SO_3$, HF—$NbF_5$, HF—$TaF_5$, $SbF_5$, HF—$SbF_5$, $SbF_5$—$FSO_3H$, $FSO_3H$—$TaF_5$, $SbF_5$—$CF_3SO_3H$). As the Lewis acid, there can be exemplified $BF_3$, $BF_3OEt_2$, $AlCl_3$, $FeCl_3$, $ZnCl_2$, $TiCl_4$, and $SnCl_2$. Included among the preferred catalysts are water-soluble catalysts.

The amount of the catalyst to be used need only be an effective amount, depending on the reaction conditions. For example, the amount of the catalyst is, relative to 100 parts by weight of the substrate of a ketoisophorone derivative (2) (e.g., KIP), about 0.001 to 100 parts by weight, preferably about 0.01 to 10 parts by weight, and more preferably about 0.1 to 5 parts by weight.

A solid catalyst (particularly, a solid acid catalyst) may also be used as the catalyst. Examples of the solid acid catalyst include strong acid ion-exchange resins (e.g., non-porous or porous ion-exchange resins containing a sulfonic acid group), superstrong acid ion-exchange resins (e.g., non-porous or porous ion-exchange resins having a superstrong acid group such as —$CF_2CF_2SO_3H$), sulfates (e.g., $CaSO_4$, $Fe_2(SO_4)_3$, $CuSO_4$, $NiSO_4$, $AlSO_4$, $MnSO_4$, $BaSO_4$, $CoSO_4$, $ZnSO_4$, $(NH_4)_2SO_4$), metal oxides (e.g., $SiO_2$, $Al_2O_3$, $TiO_2$, $Fe_2O_3$, $ZrO_2$, $SnO_2$), double or complex oxides ($SiO_2$—$Al_2O_3$, $SiO_2$—$TiO_2$, $TiO_2$—$ZrO_2$, $SiO_2$—$ZrO_2$), zeolites (e.g., zeolites of Y-type, X-type and A-type which have an acidic OH group; $ZSM_5$, mordenite, $VPI_5$, $AlPO_4$-5, $AlPO_4$-11), kaolin, and heteropolyacids (e.g., polyacids containing any of the elements P, Mo, V, W and Si).

Of the solid acid catalysts mentioned above, one example of the strong acid ion-exchange resins is styrene-divinyl benzene sulfonic acid-based ion-exchange resin (Amberlyst 15 manufactured by Organo, Ltd.), and fluorinated sulfonic acid-based resins: "Nafion NR 50" by Aldrich Chemical Company, Inc. and "Nafion H" by Dupont are examples of the superstrong acid ion-exchange resins.

The solid acid catalyst may be a solid catalyst in which a protonic acid (e.g., protonic acids such as the superstrong acids mentioned above, strong acids) or a Lewis acid is supported on a support (carrier) or a porous support.

As the substance to be supported (acid catalyst), there can be exemplified such acid catalysts as exemplified above. Concretely, $SbF_5$, $TaF_5$, $BF_3$, $AlCl_3$, $AlBr_3$, $SbF_5$—HF, $SbF_5$—$FSO_3H$, $SbF_5$—$CF_3SO_3H$, $SO_4^{2-}$, and tungstic acid, etc.

The support or carrier may be either non-porous or porous, and either will do. Examples of the carrier are metal oxides ($SiO_2$, $Al_2O_3$, $TiO_2$, $Fe_2O_3$, $ZrO_2$, $SnO_2$), double or complex oxides ($SiO_2$—$Al_2O_3$, $SiO_2$—$TiO_2$, $TiO_2$—$ZrO_2$, $SiO_2$—$ZrO_2$), zeolites, graphite, Pt-graphite, ion-exchange resins, metal sulfates, metal chlorides, metals (e.g., Pt, Au), alloys (e.g., Pt—Au, Ni—Mo, Al—Mg), polymers, salts ($SbF_3$, $AlF_3$), bauxite, active carbon, and charcoal. The surface area (e.g., 10 to 5,000 $m^2$/g), pore volume, and average pore size of the porous carrier are not particularly limited. The amount of the acid component to be supported is, for example, about 0.1 to 50% by weight, preferably about 1 to 25% by weight.

Concretely, there are exemplified $SbF_5$/$SiO_2$, $SbF_5$/$Al_2O_3$, $SbF_5$/$TiO_2$, $SbF_5$/$Fe_2O_3$, $SbF_5$/$ZrO_2$, $SbF_5$/$SnO_2$, $SbF_5$/$SiO_2$—$Al_2O_3$, $SbF_5$/$SiO_2$—$TiO_2$, $SbF_5$/$TiO_2$—$ZrO_2$, $SbF_5$/$SiO_2$—$ZrO_2$, $AlCl_3$/$CuSO_4$, $SbF_5$—HF/$Al_2O_3$, $SbF_5$—HF/$SiO_2$—$Al_2O_3$, $SbF_5$—HF/active carbon, $SbF_5$—$FSO_3H$/$Al_2O_3$, $SbF_5$—$FSO_3H$/$SiO_2$—$Al_2O_3$, $SbF_5$—$FSO_3H$/active carbon, $SO_4^{2-}$/$ZrO_2$ (zirconium sulfate), $SO_4^{2-}$/$TiO_2$ (titanium sulfate), $SO_4^{2-}$/$Fe_2O_3$, $SO_4^{2-}$/$TiO_2$—$ZrO_2$, $WO_3$/$ZrO_2$ (zirconium tungstate), and Pt/$SO_4^{2-}$/$ZrO_2$.

The amount of the solid acid catalyst to be used need only be an effective amount, depending on the reaction conditions. For example, the amount of the solid acid catalyst is, relative to 100 parts by weight of a ketoisophorone derivative (2) (e.g., KIP), about 0.1 to 1,000 parts by weight, preferably about 1 to 100 parts by weight, and more preferably about 2 to 50 parts by weight (e.g., 5 to 25 parts by weight).

The solid catalyst may be used in the form of a dispersion (slurry), and may be fed into a column within which reaction components can flow.

As the acylating agent, use can be made of acylating agents having a group corresponding to $R^1$ of the formula (1), such as an aliphatic hydrocarbon group, an alicyclic hydrocarbon group, an aromatic hydrocarbon group, or a heterocyclic group. As the acylating agent, acid anhydrides, acyl halides, enol esters and others are available.

Included among the acid anhydrides are carboxylic anhydrides, such as an acid anhydride of straight- or branched-chain $C_{1-10}$alkyl-carboxylic acids (e.g., $C_{1-8}$alkyl-carboxylic acids such as acetic acid, propionic acid, butyric acid, isobutyric acid, and valeric acid; particularly $C_{1-6}$alkyl-carboxylic acids), alicyclic carboxylic acids (e.g., $C_{3-10}$cycloalkyl-carboxylic acids such as cyclohexanecarboxylic acid), aromatic carboxylic acids ($C_{6-12}$aryl-carboxylic acids such as benzoic acid and toluic acid), halogen-containing carboxylic acids (e.g., chloroacetic acid, trichloroacetic acid, trifluoroacetic acid), heterocyclic carboxylic acids (e.g., furancarboxylic acid, thiophenecarboxylic acid, nicotinic acid, pyridinecarboxylic acid), with $C_{1-4}$alkyl-carboxylic acid anhydrides ($C_{2-4}$carboxylic acid anhydrides such as acetic anhydride and propionic anhydride) particularly preferred.

Included among the the acyl halides are those corresponding to the acid anhydrides enumerated above, such as $C_{1-10}$alkyl-carboxylic acid halides (e.g., $C_{1-8}$alkyl-carboxylic halides such as acetylchloride, propionyl chloride, butyryl chloride), alicyclic carboxylic halides (e.g., cyclohexanecarboxylic acid halide), aromatic carboxylic acid halides (e.g., benzoic acid halide), and heterocyclic carboxylic acids (e.g., furancarboxylic acid halide). $C_{1-4}$alkyl-carboxylic acid halides (e.g., $C_{2-4}$alkyl-carboxylic acid halides such as acetyl chloride and propionyl chloride) are preferred.

Included among the enol esters are isopropenyl acetate, isopropenyl propionate, isopropenyl isobutylate, isopropenyl butylate, and cyclohexenyl benzoate.

The amount of the acylating agent is at least about two times the amount of the ketoisophorone derivative (2) (e.g., KIP) in mols (e.g., 2 to 10 times in mols), preferably about three to ten times in mols. An excess of the acylating agent also serves as a solvent.

The hydroquinone diester derivative of the formula (1) (e.g., a 2,5,6-tri-substituted-hydroquinone diester derivative, particularly 2,5,6-trimethylhydroquinone diester) can be obtained at high conversion and high selectivity by reacting the compound represented by the formula (2) (particularly, 2,6,6-trimethylcyclohex-2-ene-1,4-dione) with the acylating agent.

In the present invention, the reaction may be carried out in the absence or presence of a solvent. As the solvent, there may be mentioned, for example, straight- or branched-chain saturated or unsaturated hydrocarbon-series solvents (e.g., aliphatic hydrocarbons such as hexane, heptane, and octane; alicyclic hydrocarbons such as cyclohexane; unsaturated aliphatic or alicyclic hydrocarbons such as octene and cyclohexene; aromatic hydrocarbons such as benzene, toluene, and xylene); organic acid solvents (e.g., acetic acid, propionic acid, butyric acid, lactic acid, trichloroacetic acid, trifluoroacetic acid); ester-series solvents (e.g., methyl acetate, ethyl acetate, butyl acetate); halogen-series solvents (e.g., methylene chloride, chloroform, carbon tetrachloride, 1,2-dichloroethane, chlorobenzene, dichlorobenzene); ether-series solvents (e.g., diethyl ether, diisopropyl ether, dibutyl ether, tetrahydrofuran, dioxane, ethylene glycol dimethyl ether, diethylene glycol dimethyl ether); ketone-series solvents (e.g., acetone, methyl ethyl ketone, methyl isobutyl ketone, diisobutyl ketone); and aprotic polar solvents [amide-series solvents (e.g., dimethylformamide, dimethylacetaldehydeamido); amine-series solvents (e.g., N-methylpyrrolidone); sulfoxide-series solvents (e.g., dimethyl sulfoxide); nitriles (e.g., acetonirile, benzonitrile), nitros (e.g., nitromethane, nitroethane, nitrobenzene)]. These solvents can be used either singly or in combination.

For better crystallization efficiency, the use of a smaller amount of the solvent is advantageous, and the amount of the solvent is, relative to the reaction system, about 0 to 70% by weight, preferably about 0 to 50% by weight.

In the reaction system of the present invention, the concentration of a ketoisophorone derivative (2) (e.g., KIP) as the substrate is not particularly limited, and may for example be about 5 to 50% by weight (e.g., 5 to 40% by weight), preferably about 10 to 45% by weight (10 to 35% by weight).

The reaction temperature can be selected within the range of 0 to 150° C., preferably 10 to 120° C. (e.g., 10 to 100° C.), and is usually 50 to 110° C. The reaction temperature being too high tends to cause the objection compound to be colored or the yield to decrease, and the reaction temperature being too low is likely to cause the reaction to proceed at a considerably slow rate.

The reaction can be brought to an end at a suitable stage, e.g., at a stage the conversion of the ketoisophorone reaches 95% or higher, particularly 98% or higher.

In such reaction, a catechol diester derivative (3) represented by the formula (3) is by-produced, which is the fact newly known. In the formula, $R^1$ and $R^2$ have the same meanings as defined for the formula (1).

The amount of the catechol diester derivative (3) to be by-produced varies depending on the species and amount of the catalyst and reaction conditions, and is for example about 1 to 50 mol % (particularly 4 to 15 mol %). The separation of the object compound (1) from the compound (3) is difficult, which makes efficient production of hydroquinone diester derivatives (1) of high purity difficult.

[Crystallization·Washing]

In the present invention, therefore, the object compound (1) is obtained in a high purity through crystallization from a reaction mixture and washing of the crystallized product. If necessary, the reaction mixture may be neutralized with a base, filtrated, and condensed in advance of the crystallization. The crystallization can be performed in a variety of manners. For instance, in order to provide hydroquinone diester derivatives (1) of high purity through easy and simple operations, it is advantageous to, if necessary, neutralize the reaction mixture with a base, add a solvent for crystallization (a crystallization solvent), and lower the temperature (e.g., from the reaction temperature at a point of about 50 to 120° C.) for crystallization. The regulation of the temperature of the reaction mixture for crystallization can be conducted by, for example, adding the crystallization solvent and gradually lowering the temperature of the reactor down to room temperature or below. The crystallization temperature can be selected within the range of, for example, −50° C. to 150° C., preferably about −10° C. to 100° C., and particularly about 0° C. to 80° C.

For neutralization of the reaction mixture, a variety of bases can be employed, such as strong alkalis (e.g., alkaline metal hydroxides such as sodium hydroxide and potassium hydroxide) and weak alkalis (e.g., alkaline metal carbonates such as sodium hydrogencarbonate and potassium hydrogencarbonate, and alkaline metal carbonates such as sodium carbonate). The amount of the base to be used can suitably be selected within the range of about 0.5 to 10 equivalents relative to the amount of the acid catalyst used. When a solid catalyst is employed as the catalyst, the neutralizing operation is not always necessary, and the rest (a separated liquid) of the reaction mixture from which the solid catalyst has been removed by filtration or other means, may be subjected to a crystallization step.

As the crystallization solvent, a variety of polar solvents are utilizable, such as water, alcohols (e.g., methanol, ethanol), esters (e.g., methyl acetate, ethyl acetate), ketones (e.g., acetone), ethers (e.g., dioxane, teterahydrofuran, ethylene glycol dimethyl ether), aprotic polar solvents (e.g., the amides mentioned above), organic acids (e.g., acetic acid, propionic acid, butyric acid, lactic acid, trichloroacetic acid, trifluoroacetic acid), aprotic polar solvents [amides (e.g., dimethylformamide, dimethylacetoaldehydeamide), amines (e.g., N-methylpyrrolidone), sulfoxides (e.g., dimethyl sulfoxide), nitriles (e.g., acetonitrile)], and mixed solvents thereof.

Preferred crystallization solvents are hydrophilic solvents (particularly, water, water-miscible solvents, and mixed solvents thereof). Particularly, it is preferred that crystallization is effected by adding a solvent composed of at least either an organic carboxylic acid or water (i.e., an organic solvent only, water only, and a mixed solvent of an organic carboxylic acid and water) to the reaction mixture. As the organic carboxylic acid, there can be exemplified carboxylic acids corresponding to the acrylating agent listed above, such as aliphatic carboxylic acids (e.g., $C_{1-10}$alkylcarboxylic acids such as acetic acid, propionic acid, butyric acid, isopropylcarboxylic acid), alicyclic carboxylic acids (e.g., cyclohexanecarboxylic acid), aromatic carboxylic acids (e.g., benzoic acid), and heterocyclic carboxylic acids. Preferred among the organic carboxylic acids mentioned above are water-miscible carboxylic acids, with acetic acid particularly preferred.

When an acid anhydride (e.g., acetic anhydride) is employed as the acylating agent, an organic carboxylic acid (e.g., acetic acid) is formed as a result of the reaction. The acidanhydride (e.g., acetic anhydride) left unreacted can be converted to an organic carboxylic acid (e.g., acetic acid) by adding suitable amounts of an organic carboxylic acid (e.g., acetic acid) and water after the reaction is complete, which makes the composition of the solvent system (e.g., acetic acid solution) in the reaction mixture suitably regulated for crystallization. For such reasons, in the specification, "the solvent constituting the crystallization solvent" and "the composition of the solvent" are taken to include a component(s) formed through the reaction (e.g., acetic acid) and a component(s) which is generated through the succeeding treatment (e.g., acetic acid). A process like this does not require evaporation of the reaction mixture nor freshly adding a suitable crystallization solvent, making the production process simpler.

When the solvent in the crystallization system is a mixed solvent of a polar organic solvent (e.g., organic carboxylic acids) and water, the ratio of the polar organic solvent (e.g., organic carboxylic acid) to water can be selected within a wide range, and example of which is about 20/80 to 90/10 (weight ratio), preferably about 30/70 to 80/20 (weight ratio), and more preferably about 40/60 to 70/30 (weight ratio). When the proportion of the polar organic solvent (e.g., organic carboxylic acids) in the crystallization system is too low, the amount of the by-product(s) in the crystallized product is increased. When the proportion of the polar organic solvent is too high, the yield of the objection compound is decreased. The ratio of the polar organic solvent (e.g., organic carboxylic acid) to water may be about 10/90 to 90/10 (weight ratio).

In the crystallization system, the concentration of the hydroquinone diester derivative (1) is usually about 5 to 40% by weight, preferably about 10 to 35% by weight (e.g., 15 to 35% by weight).

In the crystallizing operation, seed crystals of the hydroquinone diester derivative (1) may be added. The amount of the seed crystal to be added can be selected within a wide range of, relative to the mixture constituting the crystallization system, about 0.1 ppm to 10% by weight, preferably about 10 ppm to 5% by weight, particularly about 100 ppm to 1% by weight.

The crystallized product can easily be separated through such a conventional solid-liquid separation process (using a solid-liquid separator) as filtration (e.g., pressure filtration, suction filtration under reduced pressure) and centrifugation (e.g., centrifugal filtration).

The object compound (1) of high purity can be obtained by washing the crystallized product separated from the liquid by filtration to remove impurities therefrom. Particularly, a combination of crystallization and washing employed in the present invention causes the crystallization to be effected with high yields and enables only impurities to be removed with efficiency by washing, which provides hydroquinone diesters (1) of high purity.

For the washing, a variety of solvents that are capable of removing impurities with efficiency are employable, and those capable of eliminating catechol diester derivatives (3) with high efficiency, such as water or a mixed solvent of a water-soluble organic solvent (e.g., organic carboxylic acids typified by acetic acid, alcohols typified by methanol and ethanol, ketones typified by acetone) and water, are preferred. Washing the crystallized product with an acetic acid aqueous solution or an organic solvent such as hexane dissolves the object compound (1) out, not only lowers the yield but also further requires a step of recovering a washing liquid. This makes the production process more complicated and thus industrially disadvantageous. Therefore, the use of water is particularly preferred.

For the washing, warm or hot water of 40° C. or above (e.g., about 40 to 100° C., preferably 40 to 90° C., and more preferably about 50 to 70° C.) is preferably used. The catechol diester derivative and other impurities can be eliminated efficiently by setting the temperature of the washing liquid at 40° C. or above. Moreover, in the case of washing with warm or hot water, the biological oxygen demand (BOD) and the chemical oxygen demand (COD) of the used washing liquid are small, and this is favorable from the view point of the environment. The washing liquid at a lower temperature lowers the efficiency of elimination, and, in some cases, might have the catechol diester derivative (3) dissolving in the mother liquid precipitated out on the wettish crystals, making the separation of the object compound difficult.

The quantity of warm water to be used is, relative to 100 parts by weight of the hydroquinone diester derivative (1) contained in the crystallized product (on a dry basis), 100 parts by weight or more (e.g., about 100 to 10,000 parts by weight, preferably about 300 to 5,000 parts by weight, and more preferably about 500 to 2,000 parts by weight). Hydroquinone diester derivatives (1) of higher purity can be obtained by using 100 parts by weight of warm water or more.

After the washing, if necessary, a solid filtered out (wettish crystals) is dried. The solid can be dried by any conventional means, such as suction drying (vacuum drying), drying by heating, air drying, and combinations thereof.

The present invention is characterized in that a high-purity hydroquinone diester derivative (1) with an extremely low catechol diester content can be obtained in a high yield.

The yield of the hydroquinone diester derivative (1) is, on a solid matter basis, about 50 to 90 mol %, preferably about 60 to 85 mol %, and more preferably about 65 to 70 mol %.

The purity of the hydroquinone diester derivative (1) thus obtained is, on a solid matter basis, about 97 to 100% by weight, preferably about 98 to 100% by weight, and more preferably about 99 to 100% by weight (particularly, 99.9 to 100% by weight). The content of the catechol diester derivative (3) is, on a solid matter basis, usually about 0 to 2% by weight (e.g., 0.001 to 1.5% by weight), preferably about 0.001 to 1% by weight, and more preferably about 0.001 to 0.8% by weight.

INDUSTRIAL APPLICABILITY

Since the hydroquinone diester derivative (1) thus obtained is of high purity, it is useful particularly as an intermediate for medicines, a raw material of vitamin E, an antioxidant for higher fatty acids, higher alcohols, fats, or oils, etc.

The present invention provides high-purity hydroquinone diester derivatives efficiently. Particularly, according to the present invention, high-purity hydroquinone diester derivatives are provided in high yields through such easy operations as crystallization and washing. Moreover, through simple operations, a high-purity hydroquinone diester derivative is produced from a reaction mixture of 2,6,6-trimethylcyclohex-2-ene-1,4-dione (KIP) and an acylating agent in a high yield.

EXAMPLES

Hereinafter, the present invention will be described in further detail and should by no means be construed as defining the scope of the invention.

Example 1

A 2L glass separable flask was charged with 366 g of 2,6,6-trimethylcyclohex-2-ene-1,4-dione (KIP), 578 g of acetic anhydride, and 8 g of sulfuric acid, and a reaction was effected at 80° C. for 5 hours. Analysis by gas chromatography after completion of the reaction showed complete consumption of the starting material, 2,6,6-trimethylcyclohex-2-ene-1,4-dione (KIP) (conversion: 100 mol %), and the formation of 2,5,6-trimethylhydroquinone diacetate (DAB) in a yield of 92 mol % and 3,4,5-trimethylcatechol diacetate (DAC) in a yield of 6 mol %. The reaction mixture was neutralized with 25% by weight of a sodium hydroxide aqueous solution.

To the mixture were added 415 g of acetic acid and 680 g of water while the temperature of the mixture was kept at 80° C. (solvent composition in the crystallization system: acetic acid/water=38/62 (weight ratio)), and then the temperature of the mixture was gradually lowered from 80° C. to 25° C. to crystallize the object compound out. Thereafter, filtration was performed, and crystals filtered out was washed with 4,000 g of warm water at 60° C. The wettish crystals so obtained were vacuum-dried at 60° C. and 10 mmHg for 3 hours to provide the object compound 2,5,6-trimethylhydroquinone diacetate (DAB).

Yield: 72 mol %
Purity: 99.97% by weight
By-product DAC content: 0.03% by weight (300 ppm)
Melting point: 109 to 110° C.

Examples 2 to 4, and Comparative Example 1

Except that the temperature of warm water for the washing was varied to 20° C., 40° C., 55° C., and 80° C., the same procedure as in Example 1 was followed. The purity of the object compound 2,5,6-trimethylhydroquinone diacetate (DAB) obtained in each case is shown in Table 1. The yields were within the range of from 70 to 73 mol %.

TABLE 1

|  | Temperature of Warm Water (° C.) | Purity (%) |
| --- | --- | --- |
| Comp. Ex. 1 | 20 | 99.80 |
| Example 2 | 40 | 99.98 |
| Example 3 | 55 | 99.98 |
| Example 4 | 80 | 99.99 |

Comparative Example 2

A three-necked flask was charged with 10 g (0.066 mol) of 2,6,6-trimethylcyclohex-2-ene-1,4-dione (KIP), 20 g (0.196 mol) of acetic anhydride, and 1.14 g (6 mmol) of p-toluenesulfonic acid, and a reaction was carried out at 80° C. for 9 hours. Analysis by gas chromatography after completion of the reaction showed the conversion of 2,6,6-trimethylcycohex-2-ene-1,4-dione (KIP) at a conversion of 96 mol %, and the formation of 2,5,6-trimethylhydroquinone diacetate (DAB) in a yield of 85.1 mol % and 3,4,5-trimethylcatechol diacetate (DAC) in a yield of 7.1 mol % yield. The reaction mixture was neutralized with 3.0 ml of a 2N-sodium hydroxide aqueous solution, followed by the addition of 30 g of benzene and 30 g of water for extraction. The organic phase was condensed using an evaporator. The amount of the crude 2,5,6-trimethylhydroquinone diacetate (DAB) thus obtained was 10.1 g (yield: 65 mol %).

780 ml of hexane as a crystallization solvent was added to the condensate (crude DAB) and dissolved under reflux. Thereafter, the mixture was cooled to 10° C. for recrystallization and filtered, leaving a product filtered out. The product was washed with water and dried to give the object compound 2,5,6-trimethylhydroquinonediacetate (DAB). As shown below, the melting point of the DAB thus obtained lies within a wide range and is lower than that of pure DAB.

Yield: 41 mol %
Purity: 96.3% by weight
By-product DAC content: 2.9% by weight
Melting point: 101 to 108° C.

What is claimed is:

1. A process for producing a hydroquinone diester derivative which comprises crystallizing the hydroquinone diester derivative represented by the following formula (1):

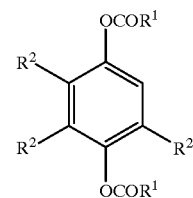

(1)

wherein $R^1$ and $R^2$ are the same or different, each representing an alkyl group, a cycloalkyl group, an aryl group, or a heterocyclic group from a reaction mixture comprising the hydroquinone diester derivative and a catechol diester derivative represented by the following formula (3):

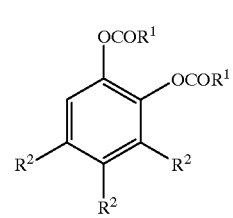

(3)

wherein $R^1$ and $R^2$ have the same meanings as defined above, and washing the crystallized product, wherein a solvent composed of an organic carboxylic acid and water is used for the crystallization.

2. A process according to claim 1, wherein the crystallized product is washed with warm or hot water of a temperature of 40° C. or above.

3. A process according to claim 1, wherein the crystallized product is washed with warm or hot water of a temperature of 40 to 100° C.

4. A process according to claim 1, wherein the organic carboxylic acid is a $C_{1-10}$alkyl-carboxylic acid.

5. A process according to claim 1, wherein the ratio of the organic carboxylic acid to water contained in the crystallization solvent is 10/90 to 90/10 (weight ratio).

6. A process according to claim 1, wherein the crystallized product is separated from the reaction mixture with a solid-liquid separator.

7. A process according to claim 1, wherein $R^1$ and $R^2$ in the formula (1) are $C_{1-4}$ alkyl groups.

8. A process according to claim 1, which comprises crystallizing the hydroquinone diester derivative from a reaction mixture which can be obtained by reacting a ketoisophorone derivative represented by the following formula (2):

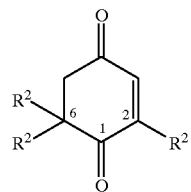

(2)

wherein $R^2$ has the same meaning as defined above with an acylating agent in the presence of a catalyst.

9. A process according to claim 8, wherein the acylating agent is a carboxylic anhydride and the hydroquinone diester derivative is crystallized with said solvent comprising an organic carboxylic acid corresponding to the carboxylic anhydride and water.

10. A process according to claim 1, wherein the crystallized product is washed to give a solid containing the catechol diester of the formula (3) in a proportion of 0 to 2% by weight on a solid matter basis.

11. A process according to claim 1, wherein the organic carboxylic acid is acetic acid.

* * * * *